United States Patent [19]

Dorsel et al.

[11] Patent Number: 5,585,639
[45] Date of Patent: Dec. 17, 1996

[54] OPTICAL SCANNING APPARATUS

[75] Inventors: Andreas Dorsel; Nicholas Sampas, both of Menlo Park, Calif.

[73] Assignee: Hewlett-Packard Company, Palo Alto, Calif.

[21] Appl. No.: 508,021

[22] Filed: Jul. 27, 1995

[51] Int. Cl.[6] .................................................. G01N 21/64
[52] U.S. Cl. .................................... 250/458.1; 250/461.1
[58] Field of Search ........................... 250/458.1, 358.1, 250/359.1, 339.11, 341.8, 461.1, 461.2; 356/311, 317

[56] References Cited

U.S. PATENT DOCUMENTS

| | | | |
|---|---|---|---|
| 4,307,930 | 12/1981 | Saito | 350/6.6 |
| 4,525,749 | 6/1985 | Maeda et al. | 358/29 |
| 4,750,045 | 6/1988 | Ohara et al. | 358/285 |
| 4,838,632 | 6/1989 | Manian | 350/6.91 |
| 4,968,892 | 11/1990 | McAtee | 250/458.1 |
| 5,006,716 | 4/1991 | Hall | 250/458.1 |
| 5,192,980 | 3/1993 | Dixon et al. | 356/326 |
| 5,218,195 | 6/1993 | Hakamata | 250/216 |
| 5,237,444 | 8/1993 | Schermer | 359/202 |
| 5,260,578 | 11/1993 | Bliton et al. | 250/461.1 |
| 5,283,433 | 2/1994 | Tsien | 250/234 |
| 5,296,700 | 3/1994 | Kumagai | 250/216 |
| 5,296,703 | 3/1994 | Tsien | 250/235 |
| 5,304,809 | 4/1994 | Wickersheim | 250/458.1 |
| 5,307,203 | 4/1994 | Hill | 359/368 |
| 5,324,633 | 6/1994 | Fodor et al. | 435/6 |
| 5,351,152 | 9/1994 | Kuo et al. | 359/376 |
| 5,381,016 | 1/1995 | Moriya | 250/458.1 |
| 5,436,717 | 7/1995 | Ogino | 250/458.1 |

*Primary Examiner*—Jack I. Berman
*Assistant Examiner*—Kiet T. Nguyen

[57] ABSTRACT

An optical scanning apparatus for scanning an array of sample regions carried on the surface of a substrate is disclosed. The apparatus includes a beam generator for generating a light beam effective to produce detectable light from such sample regions, and scanning optics for scanning the beam in one direction corresponding to a linear array of such sample regions. Light emitted from the linear array is imaged through an imaging system whose optical axis is angularly offset from the optical axis of the illumination beam, onto a photodetector. The optical configuration achieves high performance with relatively simple optics.

14 Claims, 4 Drawing Sheets

OPTICAL SCANNING APPARATUS

FIELD OF THE INVENTION

The present invention relates to an optical scanning device, and in particular, to a device for use in scanning a microarray of sample regions, such as an array of fluorescent sample regions on a substrate.

BACKGROUND OF THE INVENTION

There is a growing emphasis, in the fields of drug screening, nucleic acid sequencing and analysis, and protein engineering, on preparing and "reading" high density arrays of chemical or biological species. Such arrays can now be prepared efficiently by massive parallel schemes, such as the selective photomask techniques disclosed in U.S. Pat. No. 5,143,854. Microarrays of this type are typically formed in a planar area of between about 4–100 $mm^2$, and may have densities of up to several hundred thousand or more distinct array members/$cm^2$.

In the usual application, the members of the microarrays make up libraries of different-sequence oligonucleotides or polypeptides or small-molecule libraries with different R-group permutations, where each array sequence or permutation is position addressable, i.e., each array position corresponds to a known sequence or permutation.

In use, an array surface is reacted with one or more analytes, such as polynucleotide analytes, receptor proteins, or antiligand molecules, under conditions that promote specific, high-affinity binding of the analyte molecules to one of more of the array members. The goal is to identify one or more position-addressable members of the library array which bind to the analyte, as a method of screening for array compounds which bind to the analyte or, in the case of oligonucleotide arrays, as a method of detecting array members which can hybridize with the analyte molecule(s).

Typically, the analyte is labeled with a detectable reporter such as a fluorescent tag, which in effect can fluorescently label the one or more array regions where analyte binding to the array occurs. In relatively sophisticated schemes, two or more analytes are labeled with distinct fluorescent tags and the extent of analyte binding to the array members can be quantitated according to the level of fluorescence at array binding positions.

A variety of optical scanning devices have been proposed for reading microarrays of this type. U.S. Pat. No. 5,324,633, for example, describes a confocal fluorescence microscope device in which a laser light beam is focused by a lens system onto a small region of a substrate (beam spot less than the area of each array-member region). The same lens system is used to image fluorescence emission from the illuminated region onto a photodetector through a dichroic mirror. An X-Y movable stage functions to position each array region in the substrate successively in the illumination area of the laser beam.

Scanning confocal microscopes designed to correct chromatic aberration that occurs because of the different wavelengths of the illumination beam of fluorescence signal from the sample have also been proposed, e.g., U.S. Pat. Nos. 5,296,700 and 5,260,578. Even with relatively elaborate lens systems, however, scanning confocal microscopes have a number of inherent features that limit sample resolution and the signal-to-noise ratio achievable. The present invention is designed to overcome these limitations.

SUMMARY OF THE INVENTION

The invention includes, in one embodiment, an optical scanning apparatus for scanning an array of sample regions carried on the surface of a substrate. The apparatus has a beam generator for generating a light beam effective to produce detectable light, e.g., fluorescence emission, from the sample regions, and structure for scanning the beam in one direction corresponding to a linear array of the sample regions. An optical system in the apparatus is designed to image the light from the linear array of sample regions, in response to beam irradiation, along optical axes that are angularly offset from the corresponding optical axes of the scanning beam. The imaged light is detected by an optical detection unit.

The beam may have a beam width less than about 5 microns at the focus, and the scanning structure may be effective to move the beam a total of at least about 2–10 mm along the sample array.

The lens assembly preferably has a numerical aperture of at least about 0.25 and a scan lens with an numerical aperture of at least 0.1.

In one general embodiment, the detecting unit includes a detector surface and a slit interposed between the optical imaging system and detector surface. The imaging system is effective to image light emission from the sample array through the slit, as the beam is scanned along the one direction. Where the imaging system has a fixed optical axis, emitted light from the sample array which is off axis will produce an astigmatic image. Preferably the slit is aligned with one of the astigmatic images.

The detector may be a spatially non-resolving photodetector, or a photodetector, such as a charge-coupled device (CCD), having a one- or two-dimensional array of photosensitive elements. Where the detector is spatially resolving, the emitted light may be imaged directly onto this array, i.e., without being passed through a slit.

For scanning a two-dimensional array of sample regions, the apparatus includes structure for shifting the sample in a direction normal to the direction of beam scanning. The apparatus may further include a control unit for (i) controlling the scanning structure, (ii) recording the instantaneous position of the beam, and (iii) correlating the instantaneous positions of the beam with signals received from the detector, for constructing a map of substrate light emission levels as a function of substrate position.

These and other objects and features of the invention will become more fully apparent when the following detailed description of the invention is read in conjunction with the accompanying figures.

DETAILED DESCRIPTION OF THE INVENTION

Figure 1:
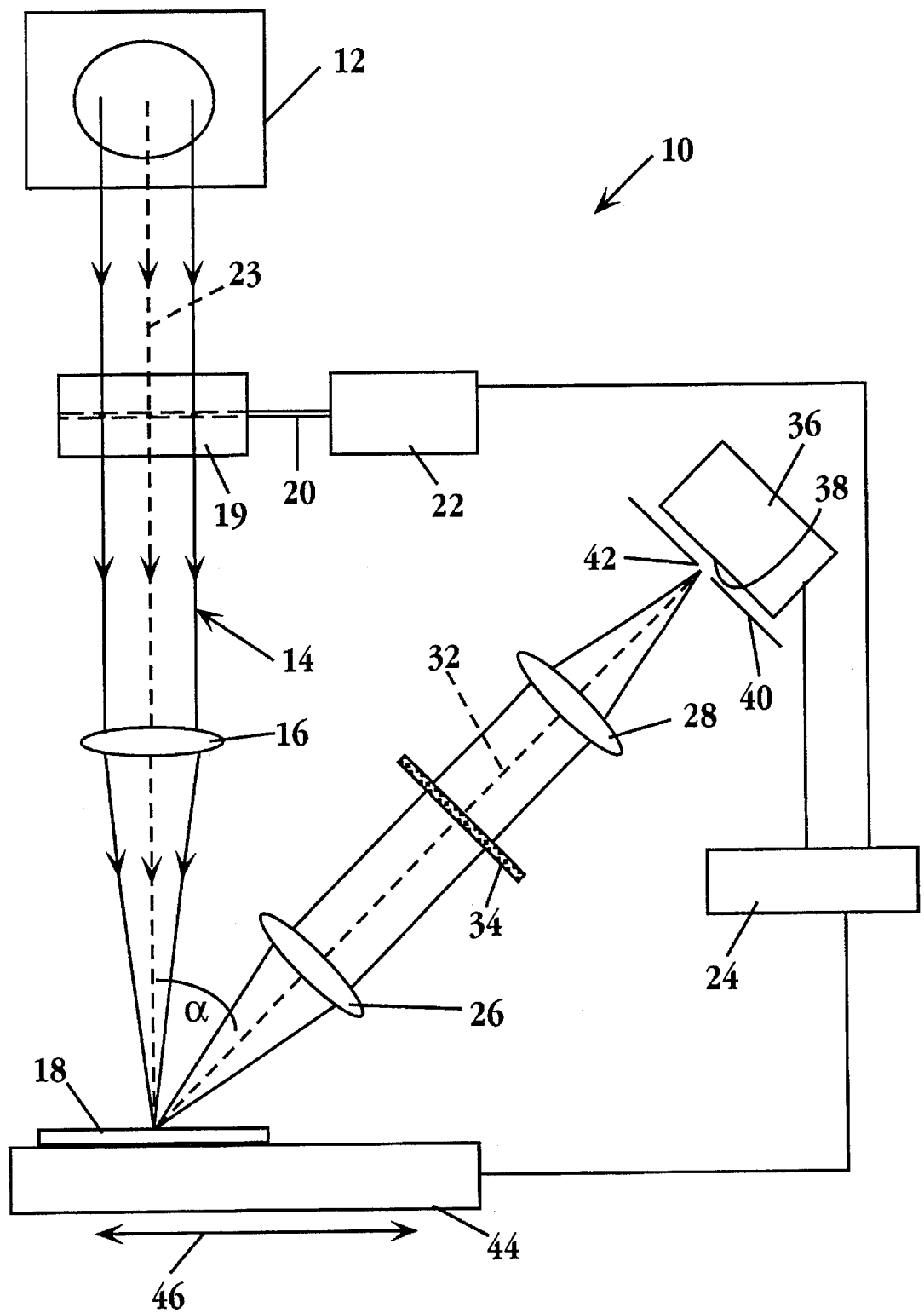
FIG. 1 is a schematic representation of an optical scanning apparatus constructed in accordance with the invention.

FIG. 1 is a schematic view of an optical scanning apparatus or microscope 10 constructed in accordance with the invention. The microscope includes a light source 12 for generating a sample-illuminating beam 14, and a lens system, indicated by lens 16, for focusing the illuminating light beam to a desired size illumination area on a sample substrate 18.

The light source in the apparatus is preferably a laser for producing a coherent light beam at a selected wavelength, typically a UV or low-visible wavelength corresponding to the fluorescence excitation wavelength of a given fluorescent sample reporter. One exemplary light source is a argon laser. The light source and focusing lens are also referred to herein, collectively, as a beam generator. The beam generator may also include a beam expander effective to match the beam diameter of the laser to a diameter more suitable for the scan lens.

Figure 2:
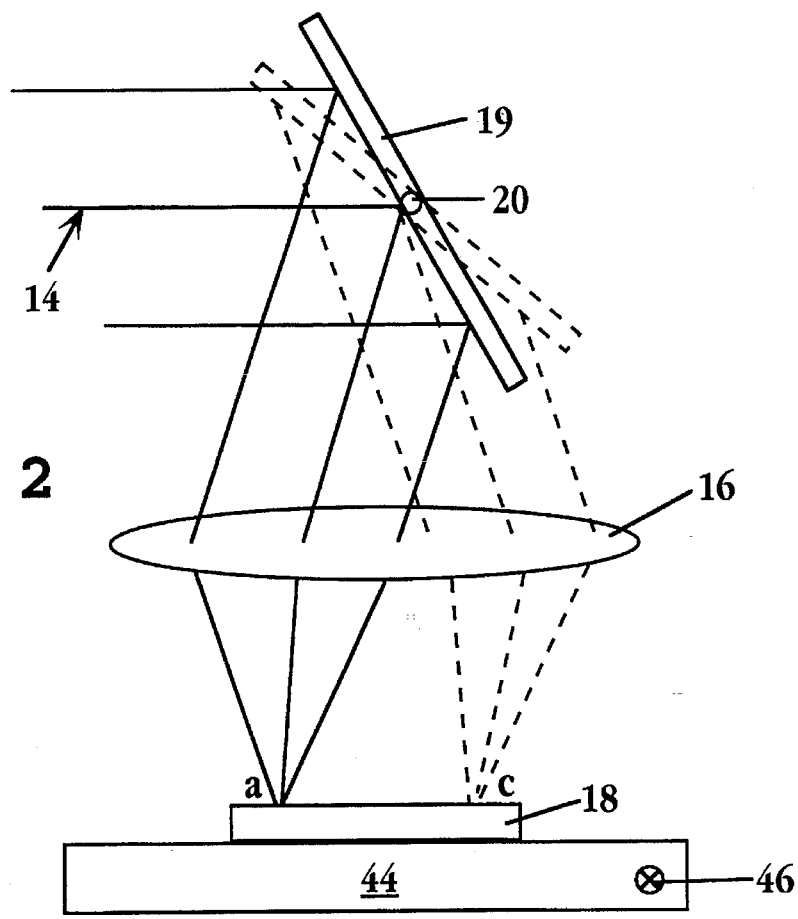
FIG. 2 is a schematic representation of components in the apparatus for scanning an illumination beam in a linear array in the sample.

With reference to FIGS. 1 and 2, light from source 12 is reflected onto the sample by a mirror 19. The mirror is pivotally mounted for angular movement about an axis 20, under the control of a motor 22, as indicated in FIG. 1. A suitable motor, such as a galvo-scanner motor, for controlling the mirror motion is also commercially available, as is a scanning mirror.

The pivoting movement of the mirror is designed to scan the beam in one direction (orthogonal to the plane of the drawing in FIG. 1, and in a left-to-right direction in FIG. 2) over a linear array of sample regions on sample 18, when motor 22 is suitably activated. In FIG. 2, the linear sample array on the sample surface lies between points a and c, corresponding to a typical scanning distance of at least 2–10 mm. Mirror movement between the positions indicated by dotted and solid lines in the figure scans the focused illumination beam between points "a" and "c" on the substrate.

With reference again to FIG. 1, the scanned beam moves in a plane 23 that intersects the linear sample array and is perpendicular to the plane of FIG. 1. In the embodiment shown, the scanning plane is normal to the surface of the sample, although oblique incident angles are also contemplated. Motor 22 is under the control of a controller/analyzer unit 24, whose operation will be described below.

Mirror 19 and its driving motor 22 are also referred to herein collectively as scanning means for scanning the light beam from source 12 in one direction corresponding to a linear array of sample regions.

The lens system represented by lens element 16 is a scan lens system, such as described in Smith, W. J., Modern Lens Design, McGraw Hill, 1992, p. 413. The lens system preferably has a numerical aperture of at least about 0.1, and may include a field-flattening lens element.

Figure 3:
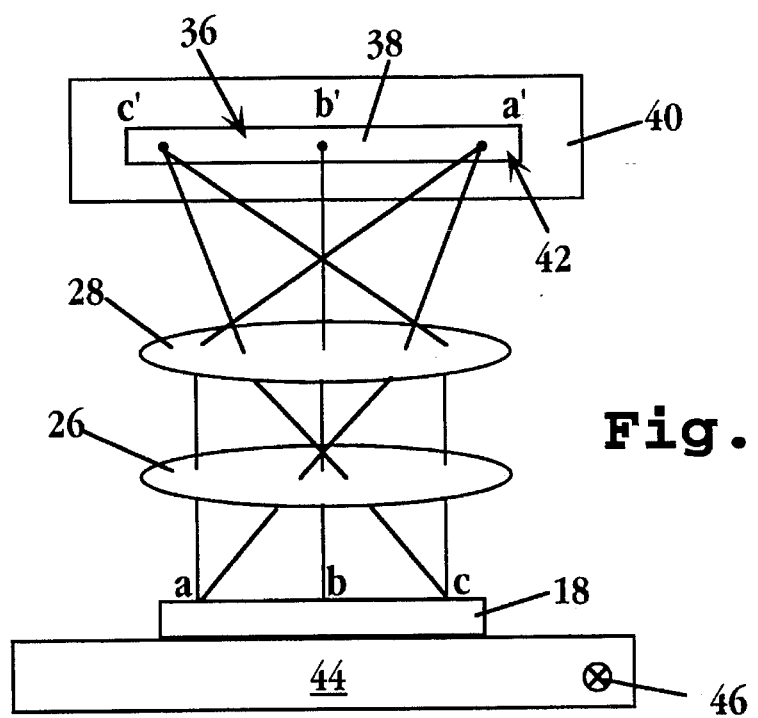
FIG. 3 is a schematic representation of components in the apparatus for detecting emitted light from a sample, as the illumination beam is scanned over a linear array in the sample.

A second or imaging lens system in the apparatus includes a collimating lens element 26, and a focusing lens element 28. As shown in FIG. 3, light rays from a given object point are collimated between lenses 26 and 28. The imaging lens system is designed to image light emitted from the sample, in response to illumination from beam 14, in an imaging plane indicated at 32. More specifically, this plane, which is normal to the plane of FIG. 1, is defined by a series of light emission axes, each representing the axis of light emitted from an illuminated region of the sample, and directed through the imaging lens system, as the illumination beam is scanned within scanning plane 23. According to an important feature of the invention, the axes defining plane 32 are angularly offset from the corresponding illumination-beam axes an angle $\alpha$, allowing separate optics for illumination and imaged-light beams.

The imaging system may also include a filter 34, such as a bandpass filter, for selectively blocking illumination-beam light reflected from the sample surface. The elements in the system, including lens elements 26, 28 and filter 34 are also referred to herein as imaging means. Of course, the filter may be one of a set of different filters, such a filter in a filter wheel, with different filters in the set optimized for the scanning of different dyes.

With reference to FIGS. 1 and 3, light from the imaging system is focused onto a detector 36 for measuring emitted light from the sample surface. In the embodiment shown, the detector is a commercial photocell having a spatially non-resolving light-detecting surface 38, for detecting and spatially integrating total light impinging on the detecting surface. One suitable detector of this type is a conventional photomultiplier tube. Alternatively, the detector may include a one- or two-dimensional arrays of light elements, such as provided in a standard charge coupled device (CCD).

Interposed between the imaging system and the detector surface, immediately adjacent the detector surface, is a plate 40 having an elongate slit 42, which functions to perform depth discrimination. The slit width is preferably between about 10 and 200 microns, and the slit length, between 2 and 20 mm. A suitable slit plate of this type is commercially available, and can be modified to spec. As seen in FIGS. 1 and 3, slit 42 is positioned and dimensioned to admit the focused imaged light from the imaging system onto the detector surface, as the illumination beam is scanned across a substrate array. Specifically, light emitted from end-regions "a" and "c" and mid-region "b" of a linear array on the substrate is directed through the slit to points "a'" and "c'", and "b'", respectively on the detector surface. The distance between end regions "a'" and "c'" in the slit corresponds roughly to the distance between points "a" and "c" on the substrate, e.g., in the range of 2–20 mm.

When imaging through a substrate at an oblique angle (angle $\alpha$ in the embodiment shown), aberrations occur even for a perfect lens. These lead to astigmatic behavior, in which the ray bundle first converges to a spot that has a minimum extension in one dimension, then to a circle of least confusion with somewhat larger, identical extension in the two dimensions orthogonal to the direction of propagation, and then to a spot with minimum extension in the other of the two dimensions. It is advantageous to focus the imaging optics such that the slit is in the plane for which the longer extensions of spot and the slit are parallel to each other, and to the scan direction.

With reference again to FIG. 1, the apparatus of the invention also includes a stage 44 on which substrate 18 is supported. The stage is movable in the direction of arrow 46 along an axis corresponding to the plane of FIG. 1, normal to the direction of scanning of the illumination beam. The stage is movable, under the control of unit 24 in increments corresponding to adjacent linear arrays in a two-dimensional array pattern on a substrate, and typically in increments in the range 1–20 microns. Microscope stages and actuators for incremental stage movement in a single direction are commercially available.

Completing the description of the apparatus, unit 24 is a microprocessor device operatively connected, as shown, to (i) motor 22, for control of the position and movement of scanning mirror 19, (ii) stage 44, for control of the position and movement of stage 44, and (iii) photodetector 36, for receiving digitized or analog detector signals related to light emission level measured by the photodetector, and illumination-beam and stage position. The operational design of the unit is conventional and will be apparent from the operation of the device, now to be described.

As indicated above, the microscope is intended for scanning a planar microarray of sample regions on a surface of the substrate, to detect and optionally, to quantitate, detectable reporter groups localized in one or more of the array regions. In the examples discussed below, the reporter groups are fluorescent reporters, although other reporters capable of producing a detectable light signal in response to beam illumination are contemplated.

As one example, the substrate microarray may be a high density, two-dimensional array of different sequence oligonucleotides whose sequences are suitable for use in sequencing by hybridization or detection of mutational forms of analyte nucleic acid. A solution of fluorescent-labeled nucleic acid analyte is placed on the microarray under selected stringency conditions, leading to hybridization of the analyte with complementary-sequence oligonucleotides in the array, and fluorescent labeling in the array regions where such binding occurs. The substrate is then washed to remove unbound and non-specifically bound analyte.

As another example, the microarray may be prepared to include a high density array of different-sequence polypeptides which collectively make up a combinatorial peptide library. To this array is added a fluorescent-labeled receptor or anti-ligand analyte which may bind with high affinity to one or more of the library members. After exposing the array surface to the labeled target, the surface is washed to remove unbound and weakly bound target, leaving fluorescent labeling at high-affinity regions of the microarray only.

Other types of one- or two-dimensional microarrays, such as small-molecule library arrays, arrays of single clonal cells, and the like are also suitable.

After fluorescent labeling, the substrate is placed on the microscope stage for scanning and fluorescence-position mapping. In the configuration shown in FIG. 4 the sample substrate is a transparent glass slide 50 having a microarray formed on its lower surface 52, and consisting of a two-dimensional array of regions, such as regions 54, 56 in the figure. Each region shown is a member of a linear array, such as array 58 containing region 56, that extends in a direction normal to the plane of the drawing.

Figure 4:
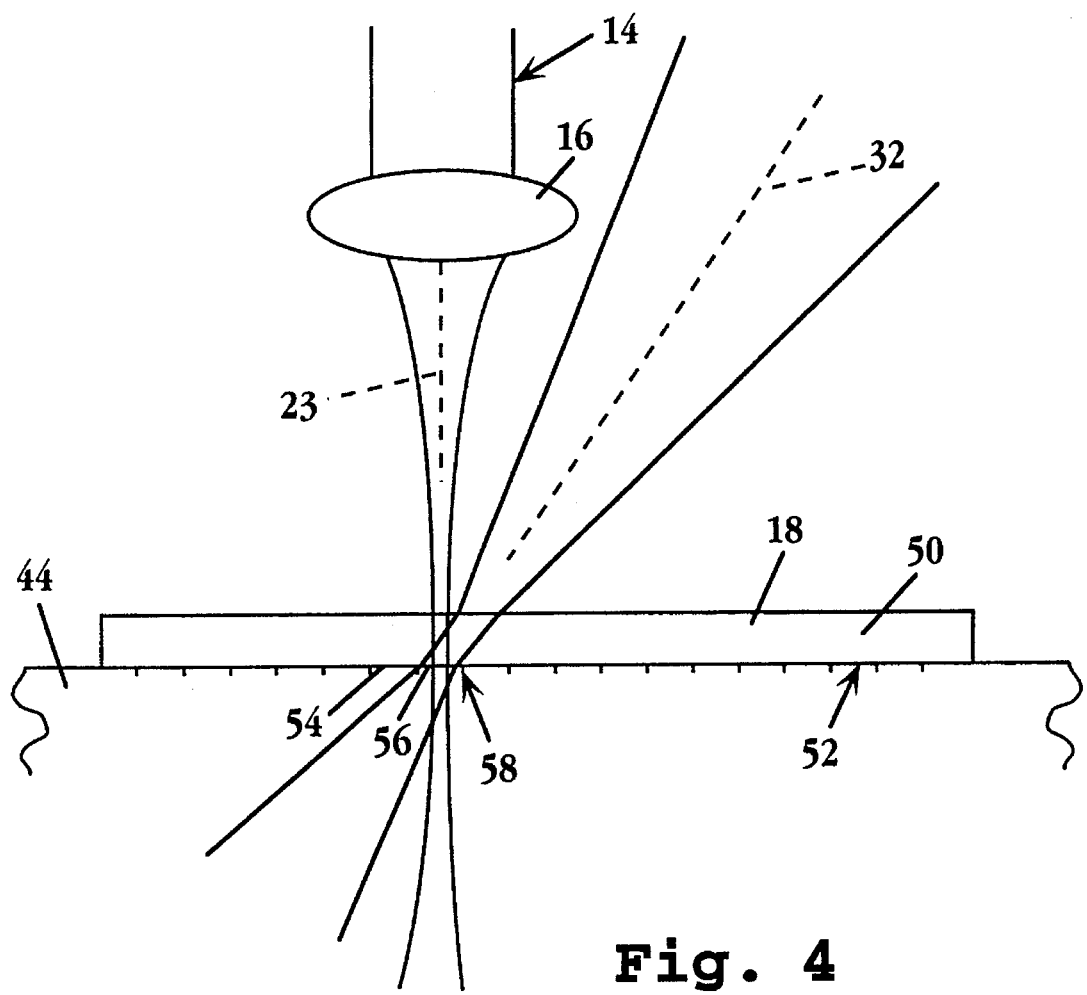
FIG. 4 shows sample regions of light-beam excitation and light-emission detection in the apparatus.

The beam diagrams in FIG. 4 illustrate several features of the invention. First, the illumination beam may be focused by lens 16 to achieve high resolution, meaning that the illumination spot at the plane of the microarray is substantially smaller than the dimensions of an array region. High beam resolution can be achieved in the present invention with relatively inexpensive monochromatic optics having a numerical aperture of about 0.1 or more.

Figure 5:
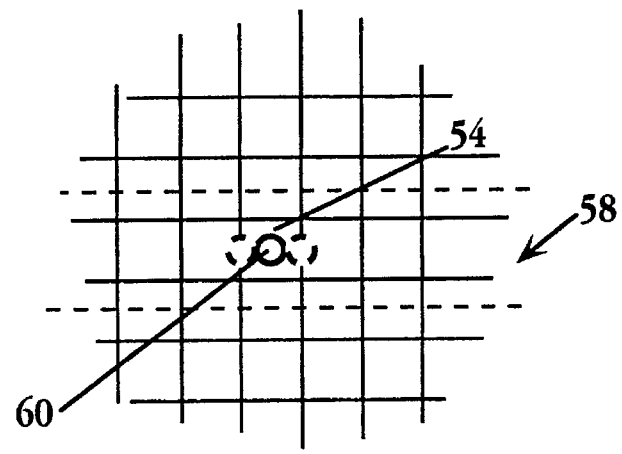
FIG. 5 is a plan view of a portion of a sample, illustrating an array of distinct sample regions, and showing movement of the excitation beam through a sample region in a scanning direction.
Figure 6:
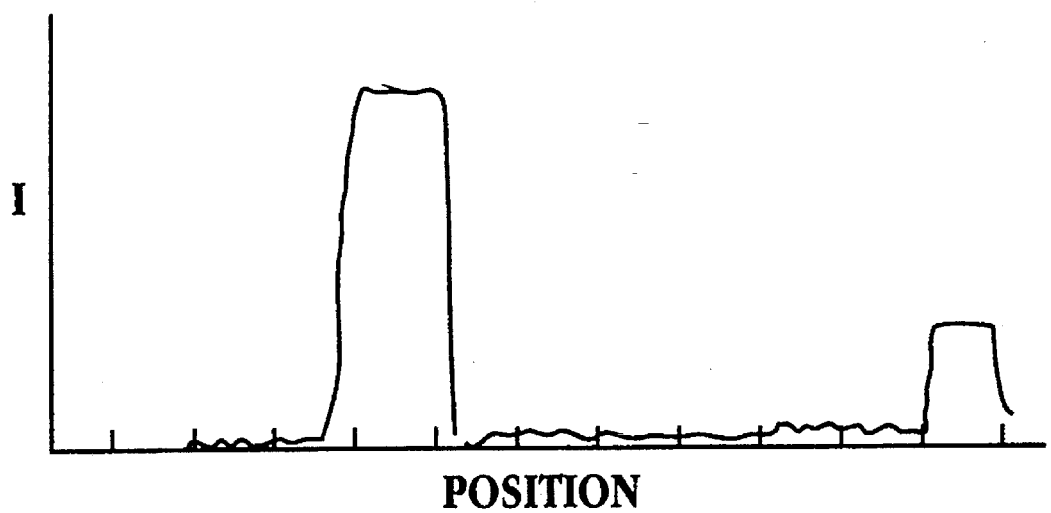
FIG. 6 is a plot showing measured light emission from a sample as an excitation beam is scanned over a linear array of regions in the sample.

The ability of a small beam spot to improve resolution and quantitation of light emission from an array region is illustrated in FIG. 5, which shows movement of focused illumination beam 60 into and through a region 54 along a linear array 58. Typical dimensions for the beam spot are 5 microns or less, and dimensions for each array region are 10–20 microns. As seen, the beam will pass through several positions in which it is completely localized within the region, as well as position of overlap with adjacent positions. As a result, an emitted light profile with a substantially rectangular shape, such as shown in FIG. 6 can be obtained. The amount of bound fluorescent label in each labeled region can be quantitated by integrating the area under each peak. The spatial integrating may be done by the detector, in the case of a spatially non-resolving light detector, or by unit 24, receiving digitized light information from the detector. In the example shown in FIG. 6, the light intensity ratio of the two peaks in the scanned linear array is about 3:1.

With reference again to FIG. 4, it is appreciated that since the imaging optics is independent of the illumination beam optics, the imaging optics can be independently designed and focused to optimize light collection from the illuminated substrate regions. In particular, the resolution area of the imaging optics at the microarray surface can encompass the entire illumination beam spot without loss of resolution. At the same time, the imaging optics can have a relatively large numerical aperture, e.g., greater than 0.25, to enhance emitted light intensity at the detector. In addition, there is no need for special lens components to reduce chromatic aberration, since the imaging system is designed to focus imaged monochromatic light only. Further, since only minor amounts of stray scattered illumination-beam light reach the imaging system, this light can be removed by light filtering without significant loss of emitted light.

In a typical scanning operation, the stage is moved to position the scanning plane to correspond to one of the linear arrays, such as array 58. The illumination beam is now scanned across the linear array in scanning plane 23, exciting fluorescence light emission in each region in the array where labeled analyte is bound. The emitted light is imaged onto the photodetector, through slit 42, and the intensity of light emission is measured. The measured intensity associated with each mirror position, or alternatively, with each sensing element in a multi-element photodetector, is recorded and stored with the associated region in the scanning plane in unit 24.

After the regions in a linear array are scanned, the stage is moved to place the scanning plane to correspond to the next linear array, and this array is now scanned and recorded as above.

As indicated above, the position of the stage and the position and movement of scanning mirror 19 is under the control of unit 24, which records the instantaneous microarray position under illumination. This position is stored with the corresponding light-intensity value associated with each microarray position, for purposes of constructing an illumination map of the microarray. Alternatively, or in addition, the position of the scanning beam along the linear array of regions being scanned can be determined from the position of the light-sensing element receiving emitted light, where the photodetector has an array of such elements.

Figure 7:
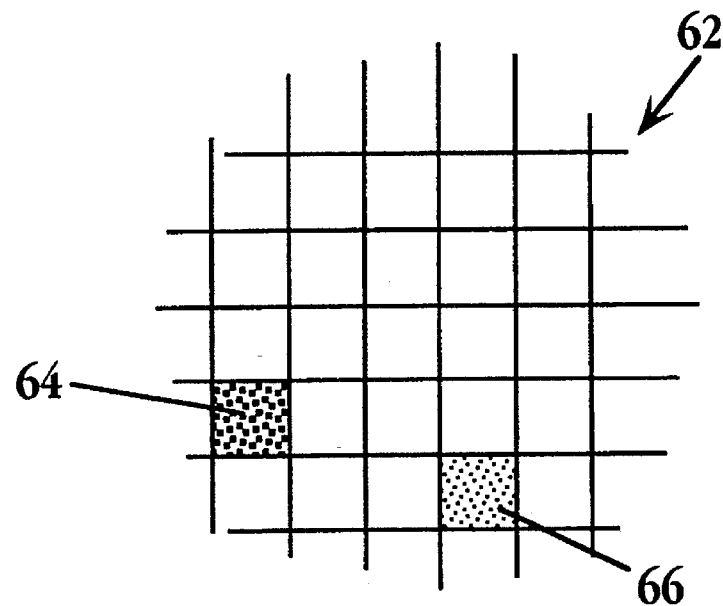
FIG. 7 illustrates a portion of a sample array map constructed from sample emission patterns, in accordance with the invention.

After an array has been scanned, unit 24 outputs an array map showing the light intensity associated with each region in the array. FIG. 7 shows a typical intensity map for a portion of a two-dimensional array 62, where the shading level in fluorescent regions 64, 66 in the array is related to the total integrated light intensity measured at the associated array region. The output may also include the identity of the molecular species at which fluorescence signal was observed or, in the case of sequencing by hybridization, analyte sequence information.

While the invention has been described with respect to specific embodiments and applications, it will be appreciated that various changes and modifications may be made without departing from the invention.

What is claimed:

1. An optical scanning apparatus for scanning an array of sample regions carried on a surface of a substrate, comprising:

a beam generator for generating a light beam effective to produce detectable light from such sample regions, means for scanning said beam in one direction corresponding to a linear array of such sample regions, means for imaging light corresponding to light from said linear array of sample regions in response to beam irradiation, where the optical axes of the imaged light, as the beam is scanned in said one direction, (i) are angularly offset from the corresponding optical axes of the light beam, and (ii) intersect the optical axes of the light beam at a surface plane corresponding to the sample regions along said linear array, detection means for detecting said imaged light from said imaging means, wherein said detection means includes a detector surface and a slit interposed between the imaging means and the detector surface, and said imaging means is effective to image light emission from said sample array through said slit, as said beam is scanned in said one direction.

2. The apparatus of claim 1, wherein said imaging means produces an astigmatic image oriented parallel to said slit, as said beam is scanned across said sample array in said one direction, and said slit is in a plane coincident with said astigmatic image.

3. The apparatus of claim 1, wherein said slit is straight.

4. The apparatus of claim 3, wherein said imaging means includes a lens assembly with a numerical aperture of at least about 0.25.

5. The apparatus of claim 1, wherein said beam has a beam width less than about 5 microns at the focus, and said scanning means is effective to move said beam a total of at least about 10 mm in said one direction.

6. The apparatus of claim 1, wherein said scanning means scans a two-dimensional array of sample regions, and which further includes means for shifting said sample in a direction normal to the direction of beam scanning.

7. The apparatus of claim 1, for scanning an array of sample regions carried on a surface of a transparent substrate, wherein said beam is adapted to impinge upon sample regions on said sample surface through the substrate, and said imaging means is adapted to image light received through the substrate.

8. The apparatus of claim 1, wherein said beam is effective to excite sample fluorescence emission at a selected wavelength, and said detector is effective to detect fluorescence emission at a longer wavelength.

9. The apparatus of claim 8, wherein said detector is a spatially non-resolving detector.

10. The apparatus of claim 1, which further includes control means for (i) controlling said scanning means, (ii) recording the instantaneous position of said beam, and (iii) correlating the instantaneous positions of said beam with signals received from said detector, whereby a map of substrate light emission levels as a function of substrate position can be constructed.

11. An optical scanning apparatus for scanning an array of fluorescent sample regions carried on a surface of a substrate, comprising:

a beam generator for generating a light beam effective to excite fluorescence light emission from said sample regions, said beam having a beam width less than about 5 microns, means for scanning said beam, over a scanning distance of at least about 2–10 mm, in one direction corresponding to a linear array of said sample regions, a lens assembly for imaging, with a numerical aperture of at least about 0.25, fluorescence light emission corresponding to light emission from said linear array of sample regions in response to beam excitation, where the optical axes of the imaged light emission, as the beam is scanned in said one direction, are (i) angularly offset from the corresponding optical axes of the scanned beam, and (ii) intersect the optical axes of the light beam at a surface plane corresponding the sample regions along said linear array, detection means for detecting said imaged light from said lens assembly, wherein said detection means includes a detector surface and a slit interposed between the lens assembly and the detector surface, and said lens assembly is effective to image light emission from said sample array through said slit, as said beam is scanned in said one direction, shifting means for relatively shifting said sample in a direction normal to the direction of beam scanning in the plane of the sample, and control means for (i) controlling said scanning means, (ii) recording the instantaneous position of said beam, and (iii) correlating the instantaneous positions of said beam with signals received from said detector, whereby a map of substrate light emission levels as a function of substrate position can be constructed.

12. The apparatus of claim 11, wherein said lens assembly produces an astigmatic image oriented in the direction of said slit, as said beam is scanned across said sample array in said one direction, and said slit is in a plane coincident with said astigmatic image.

13. The apparatus of claim 11, for scanning an array of sample regions carried on a surface of a transparent substrate, wherein said beam is adapted to impinge upon sample regions on said sample surface through the substrate, and said lens assembly is adapted to image light received through the substrate.

14. The apparatus of claim 11, wherein said detector is a spatially non-resolving detector.

* * * * *